United States Patent [19]

Chiou et al.

[11] Patent Number: 5,328,842
[45] Date of Patent: Jul. 12, 1994

[54] COMPOUNDS, VECTORS AND METHODS FOR EXPRESSING HUMAN, CYTOSOLIC PHOSPHOLIPASE $A_2$

[75] Inventors: Xue-Chiou C. Chiou, Greenwood; JoAnn Hoskins, Indianapolis; Ruth M. Kramer, Indianapolis; John D. Sharp, Indianapolis; Donald L. White, Indianapolis, all of Ind.

[73] Assignee: Eli Lilly and Company, Indianapolis, Ind.

[21] Appl. No.: 46,508

[22] Filed: Apr. 12, 1993

Related U.S. Application Data

[63] Continuation of Ser. No. 686,558, Apr. 17, 1991, abandoned.

[51] Int. Cl.$^5$ ............... C12N 15/55; C12N 15/70; C12N 15/85
[52] U.S. Cl. ................. 435/240.2; 435/69.1; 435/70.3; 435/71.2; 435/198; 435/172.3; 435/252.3; 435/252.33; 435/320.1; 536/23.2; 935/14; 935/29; 935/32; 935/56; 935/70; 935/71; 935/73
[58] Field of Search ............ 435/69.1, 20.3, 71.2, 435/198, 172.3, 252.3, 252.33, 240.2, 320.1; 536/23.2; 935/14, 29, 32, 56, 70, 71, 73

[56] References Cited
FOREIGN PATENT DOCUMENTS

WO89/01773  1/1989  PCT Int'l Appl. .
WO89/09818  7/1989  PCT Int'l Appl. .

OTHER PUBLICATIONS

Kramer, et al., The Journal of Biological Chemistry, vol. 264, No. 10, pp. 5768-5775 (1989).
Diez and Mong, The Journal of Biological Chemistry, vol. 265, No. 24, pp. 14654-14661 (1990).
Clark, et al., Proceedings of the National Academy for Science, vol. 87, pp. 7708-7712 (1990).
Clark, et al., Journal of Cellular Biochemistry, Supplement 15B, #D308 (1991).
Leslie, et al., The FASEB Journal, vol. 4, No. 7, (1990).
Gronich, et al., The FASEB Journal, vol. 4, No. 7 (1990).
Kramer, et al., The Journal of Biological Chemistry, vol. 266, No. 8, pp. 5268-5272 (1991).
Belyavsky et al., "PCR-based cDNA Library construction . . . " Nuc. Acids. Res. 17:2919-2932 (Apr. 1989).
Berger et al. (eds) "Guide to Molecular Cloning Techniques" Methods in Enzymology 152:432-447, 661-704 (1987).
Deutscher (ed.) "Guide to Protein Purification" Methods in Enzymology 182:602-613, 738-751 (1990).
Shapiro (ed.) "Mobile Genetic Elements" Chapter 4 pp. 159-221.

Primary Examiner—Robert A. Wax
Assistant Examiner—Rebecca Prouty
Attorney, Agent, or Firm—Ronald S. Maciak; Leroy Whitaker

[57] ABSTRACT

The invention includes recombinant DNA compounds, vectors and methods useful for expressing an exceptionally rare, human, cytosolic phospholipase $A_2$ (cPLA$_2$) enzyme. The invention also includes a method for screening compounds to identify inhibitors of cPLA$_2$ which is believed to partake in several disease processes.

21 Claims, 9 Drawing Sheets

COMPOUNDS, VECTORS AND METHODS FOR EXPRESSING HUMAN, CYTOSOLIC PHOSPHOLIPASE A₂

This application is a continuation of application Ser. No. 07/686,558, filed on Apr. 17, 1991, now abandoned.

TECHNICAL FIELD OF INVENTION

The invention belongs to the general field of molecular biology and includes recombinant DNA compounds, vectors and methods useful for expressing an exceptionally rare, human, cytosolic phospholipase A₂ (cPLA₂) enzyme. The invention also includes a method for screening compounds to identify inhibitors of cPLA₂.

BACKGROUND OF THE INVENTION

Before the present invention, there was no facile method for obtaining cPLA₂ in substantial quantities. Human cPLA₂ and a method of purification is described in U.S. patent application Ser. No. 07/573,513. Antibodies reactive with cPLA₂ and methods for isolating and identifying cPLA₂ are described in U.S. patent application Ser. No. 07/663,335. At best those methods are capable of providing only limited amounts of cPLA₂ because of its scarcity in the cytoplasm of cells which naturally contain it. To illustrate the extremely rare nature of cPLA₂ and to highlight the problem solved by this invention, it need only be mentioned that less than 100 ugs of cPLA₂ exists in all of the cells present in an 80 liter culture of a human monocytic cell line. Thus, the present invention overcomes the difficulties of obtaining relatively large amounts of this rare and important enzyme.

Phospholipase A₂ (PLA₂) is the common name for phosphatide 2-acylhydrolase which catalyzes the hydrolysis of the sn-2 acyl ester bond of phosphoglycerides producing equimolar amounts of lysophospholipids and free fatty acids (Dennis, E. A., *The Enzymes* Vol. 16, Academic Press, New York,(1983)). Phospholipase A₂ enzymes are found in all living species and form a diverse family of enzymes. Of those studied to date, the vast majority have a molecular weight of approximately 14 kDa, and their amino acid sequences show great homology.

The most abundant and commonly studied PLA₂ enzymes are the secreted forms. These enzymes are produced within the cell, packaged into secretory vesicles and later released into the extracellular environment where they aid in the digestion of biological material. In contrast, cPLA₂ is found in vanishingly small amounts, remains within the cell and serves in an entirely different capacity than the secreted forms. Thorough investigation of intracellular PLA₂s has been hampered by the extremely low concentration of these enzymes in cells (Vadas and Pruzanski, *Lab. Investigation*, 55, 4: 391 (1986)).

The ability to modulate receptor mediated cPLA₂ activity via specific inhibitors is a desirable goal and may lead to new therapies for the treatment of asthma, ischemia, arthritis, septic shock, and inflammatory diseases of the skin. The inactivation or specific inhibition of cPLA₂ activity associated with particular disease states will be of great use to the medical community. To accomplish this goal, cPLA₂ presumed to be involved in the pathogenesis of certain diseases must first be identified and isolated. This has been done and was described in an earlier filed U.S. patent application mentioned above. The present invention provides genes which encode cPLA₂, vectors and host cells which are useful for expressing cPLA₂ and methods for expressing cPLA₂.

SUMMARY OF THE INVENTION

The present invention encompasses cPLA₂ genes comprising a recombinant DNA sequence that encodes a protein having the amino acid sequence of SEQ ID NO:2 as well as vectors and host cells that comprise the DNA sequence. Also encompassed in the invention is a method of using a cPLA₂ gene comprising transforming a cell with an expression vector comprising a cPLA₂-encoding gene. Another embodiment of the invention is a method of using a cPLA₂ gene comprising culturing a cell transformed by a cPLA₂ expression vector in a suitable growth medium and isolating cPLA₂ from said cultured cell. The invention also includes a method of using a cPLA₂-encoding gene to screen drugs comprising contacting the isolated cPLA₂ enzyme with a compound suspected of being able to inhibit the enzymatic activity of said cPLA₂ and determining whether the cPLA₂ enzymatic activity has been inhibited by the compound.

DETAILED DESCRIPTION OF THE INVENTION

Figure 1:
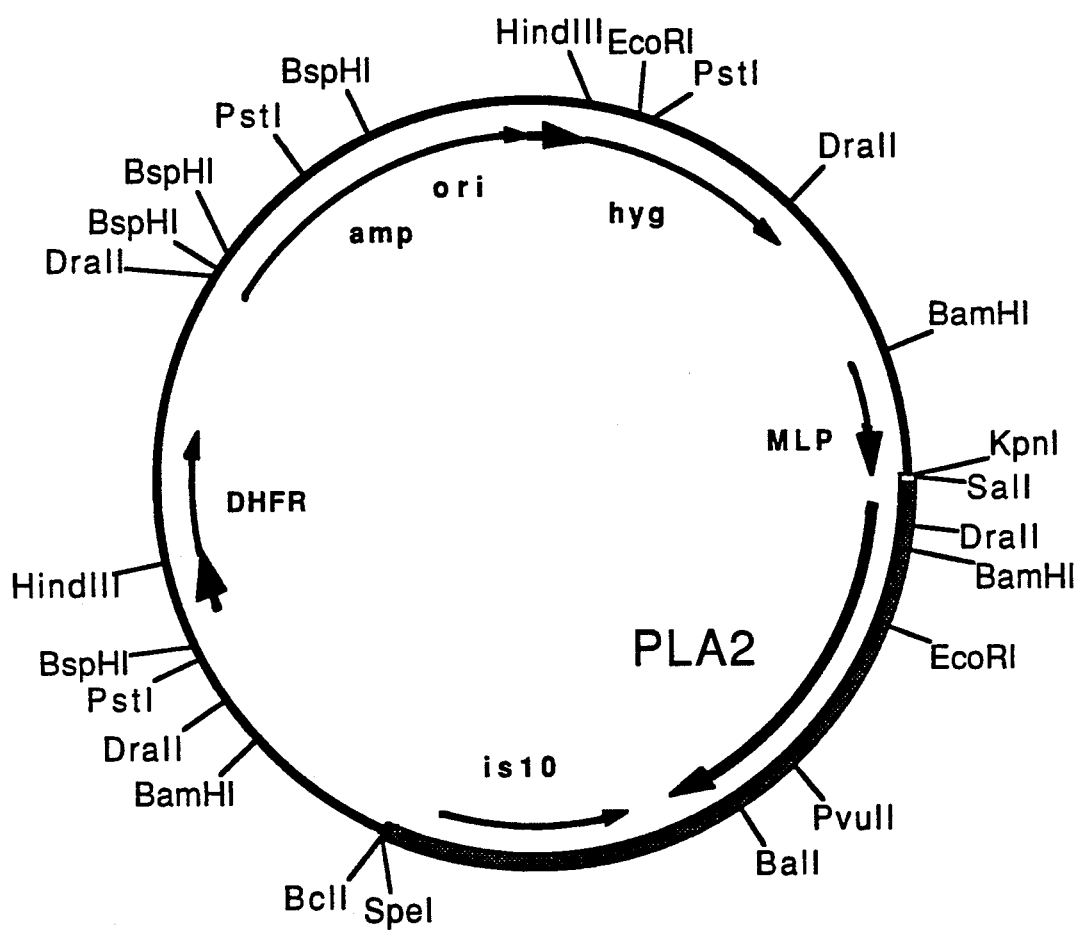
FIG. 1 is a restriction site and function map of pHDCPF.
Figure 2:
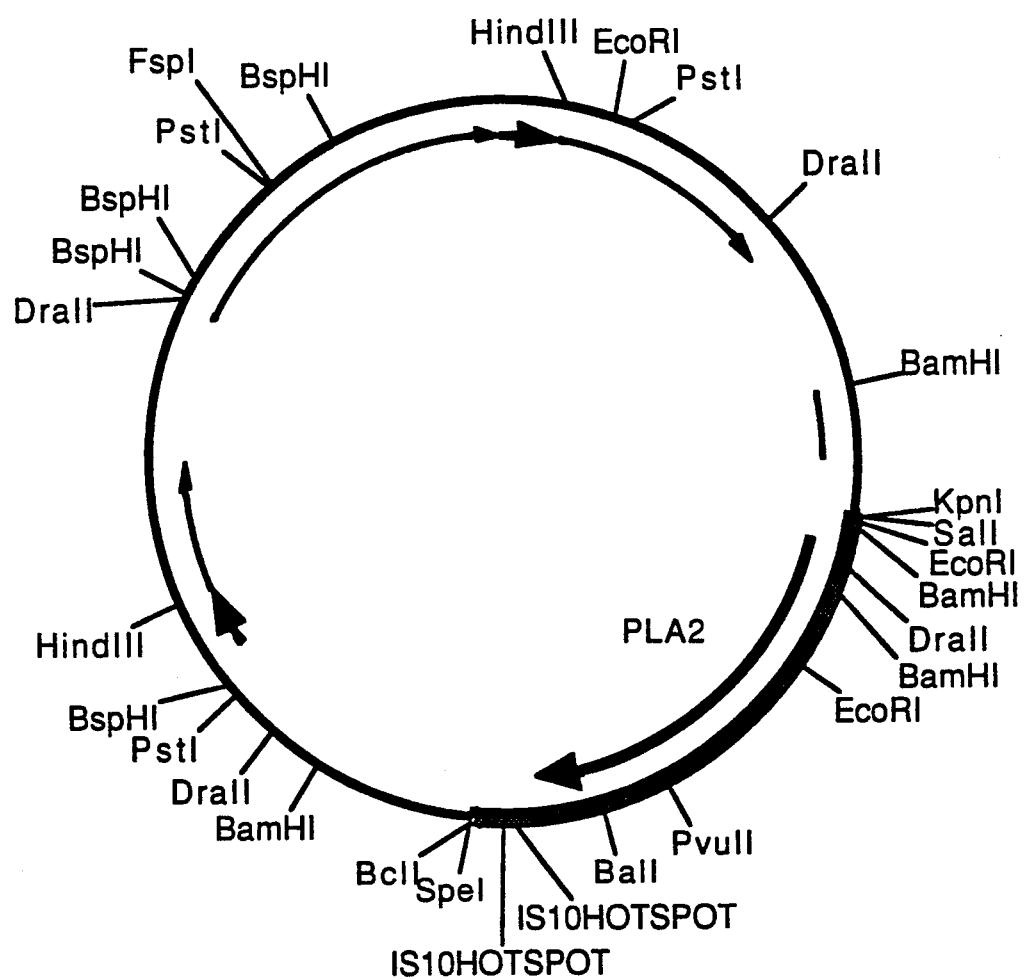
FIG. 2 is a restriction site and function map of pHDCPFS.
Figure 3:
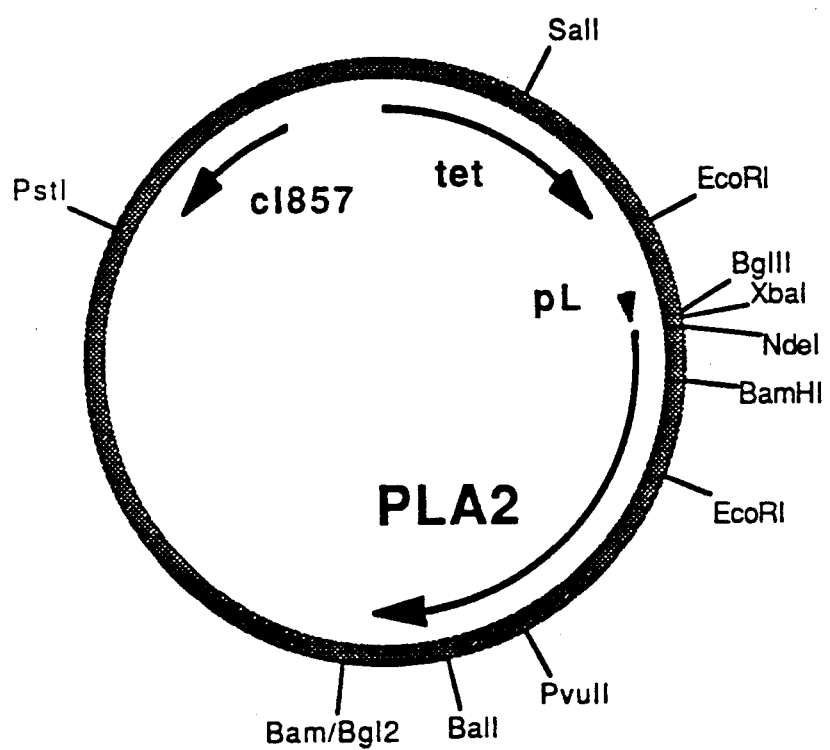
FIG. 3 is a restriction site and function map of pECPLA21.

The heart of this invention is the isolated, purified human cPLA₂ cDNA which was enzymatically copied from the messenger RNA as found in nature. Its DNA sequence is given in SEQ. ID. NO:1, and the amino acid sequence which it encodes is laid out in SEQ. ID. NO:2. Based on the degeneracy of the genetic code, those skilled in the art will recognize that many other nucleotide sequences of the same length are capable of encoding the cPLA₂ enzyme. All such sequences are also a part of the invention due to information which the natural sequence inherently contains.

The invention as a whole comprises cPLA₂-encoding DNA sequences, recombinant DNA vectors, recombinant host cells and methods of use. Each of the above embodiments is limited by the protein sequence encoded by the claimed DNA sequences. However, those skilled in the art will recognize that heterologous proteins often undergo enzymatic digestion when expressed in foreign host cells. For example, it is well known that N-terminal methionine residues, preceding a serine residue, are often removed by certain enzymes in prokaryotic cells and as such are contemplated in this invention. Moreover, the invention is not limited by the illustrations and examples used to help describe the invention.

For purposes of this document, a recombinant DNA vector can also be referred to as simply a vector. Both terms include two types of vectors, cloning and expression vectors. A cloning vector, as those skilled in the art know, is a plasmid capable of replication in an appropriate host cell. An expression vector is a plasmid capable of having a particular protein coding sequence in the plasmid transcribed and translated into a polypeptide. Both vectors preferably contain a selectable marker such as an antibiotic resistance gene which permits only transformed cells to grow in a selective medium.

In one embodiment, the invention provides recombinant DNA cloning vectors containing cPLA$_2$-encoding DNA sequences. Those skilled in the art will readily appreciate the utility of such vectors as a means for obtaining a cPLA$_2$ gene, propagating it, constructing other useful recombinant DNA vectors, and using those vectors for a variety of purposes.

Another embodiment includes recombinant DNA expression vectors useful for obtaining substantial amounts of the heretofore extremely rare cPLA$_2$ enzyme. Given the cPLA$_2$-encoding DNA sequences of the invention, those skilled in the art will be readily able to construct expression vectors using known functional elements. Four typical expression vectors are described below to help illustrate this aspect of the invention. The following vectors are described only for illustrative purposes and are not meant to limit the invention in any way.

Two different strains of E. coli were transformed with four expression vectors, and the resulting recombinant host cells were deposited with the Northern Regional Research Laboratories (NRRL) under the terms of the Budapest Treaty. Each vector has the functional elements necessary for replication in its host cell strain, thus constituting cloning vectors. Two of the deposited vectors also function as prokaryotic expression vectors, and two function as eukaryotic expression vectors. Each vector will be discussed in turn.

Plasmid pECPLA21, NRRL accession number 18774, was used to transform E. coli strain K12 DH5 alpha. The DNA sequence of SEQ. ID. NO:1 is the cPLA$_2$-encoding portion of the vector. The vector also contains an origin of replication sequence, a tetracycline resistance-conferring (tet) sequence, a temperature sensitive repressor (cI857) that regulates an inducible promoter sequence ($P_L$), and a transcription termination sequence, all of E. coli or lambda phage origin. The aforementioned functional elements of the plasmid enable the host cell to replicate numerous copies of the plasmid and, upon induction, to transcribe and translate the cPLA$_2$ gene. Those skilled in the art will of course realize that numerous other sequences having like functions may be substituted for those actually used in pECPLA21.

Plasmid pECPLA22, NRRL accession number 18775, is believed to be identical to pECPLA21. However, since it arose from a different clone, it is possible that it differs from pECPLA21 by a few base pairs, particularly in the splicing regions. Nonetheless, pECPLA22 is functionally indistinguishable from pECPLA21 in that it contains an origin of replication sequence, a tet gene, the cI857 temperature sensitive repressor that regulates the $P_L$ inducible promoter sequence, and a transcription termination sequence as well as DNA SEQ. ID. NO:1. A different strain of E. coli (E. coli K12×E. coli B hybrid RR1) was transformed with pECPLA22 in hope of gaining expression advantages over the previously discussed transformed strain. To date, both transformed E. coli strains appear equivalent with respect to expression and handling properties.

Two different eukaryotic expression vectors, pHDCPF and pHDCPFS, were constructed around SEQ. ID. NO:1. The vectors are identical except that pHDCPF contains the IS10 bacterial insertion sequence 3' to SEQ. ID. NO:1.

The IS10 insertion sequence appeared in the 3' noncoding region of the cPLA$_2$ cDNA, producing a plasmid that appeared to be a more stable form than the form lacking IS10. IS10 is well known (Hailing, S. M, and Kleckner, N., Cell, 28, 155 (1982)) and inserts into preferred nine base-pair sites in DNA, two of which appear in the 3' noncoding region of the cPLA$_2$ gene. Since it was not certain whether IS10 would affect the level of cPLA$_2$ synthesis, the insertion sequence was eliminated along with both nine base-pair sites in the bacterial expression vectors pECPLA21 and pECPLA22. However, IS10 was included in the eukaryotic expression vector pHDCPF.

Both eukaryotic expression vectors were derived from the same precursor, plasmid pHD. As such, the functional elements of pHD will be discussed and will apply equally to both pHDCPF and pHDCPFS.

The pHD vector contains an E. coli origin of replication and an ampicillin resistance-conferring gene (amp). These elements make it possible for plasmid pHD to function as a cloning vector in E. coli . As discussed previously, the skilled artisan knows that many other sequences are capable of conferring the same properties on a given vector and are routinely substituted for one another based on what is appropriate under the circumstances. For example, the present embodiment is not limited to the amp gene as the selectable marker since many other comparable markers are well-known and used in the art. Other antibiotic resistance-conferring genes such as the tetracycline and kanamycin resistance-conferring genes would also be compatible with the present invention.

The vector also contains two other selectable markers which allows the isolation of eukaryotic clones transformed by the vector. The hygromycin resistance gene (hyg) gives those eukaryotic cells transformed by the vector the ability to grow in medium containing hygromycin at concentrations which inhibit the growth of non-transformed cells, approximately 200 to 400 ug/ml. The other selectable marker which can also be used to amplify expression is the murine dihydrofolate reductase (DHRF) gene. This gene is known in the art and enables eukaryotic cells to be selected based on resistance to approximately 0.5 to 130 uM methotrexate.

In the pHD vector, the adenovirus-2 major late promoter (MLP) drives expression of the gene of interest, cPLA$_2$ in this case. Those skilled in the art can readily imagine numerous other eukaryotic promoters that could function in place of MLP. Examples include, but are not limited to, the SV40 early and late promoters, the estrogen-inducible chicken ovalbumin gene promoter, the promoters of the interferon genes, the glucocorticoid-inducible tyrosine aminotransferase gene promoter, the thymidine kinase gene promoter and the adenovirus early promoter.

Preferred cPLA$_2$ cloning vectors of the invention are those which function in *E. coli*. Preferred prokaryotic cPLA$_2$ vectors are the type which operate as both cloning and expression vectors. More highly preferred prokaryotic cPLA$_2$ vectors are pECPLA21 and pECPLA22. Preferred eukaryotic cPLA$_2$ vectors are those which function as cloning vectors in *E. coli* and also are able to operate as expression vectors in eukaryotic cells. More preferred eukaryotic cPLA$_2$ vectors have the same properties as the preferred type with the added feature that they function as expression vectors in mammalian cells. More highly preferred eukaryotic cPLA$_2$ vectors are pHDCPF and pHDCPFS and the most highly preferred is pHDCPFS.

An additional embodiment of the invention includes various types of recombinant DNA host cells. For purposes of this document recombinant DNA host cells may be referred to as recombinant host cells or simply host cells. A recombinant host cell is a cell whose genome has been altered by the addition of foreign DNA. The most common type of host cell is one that has been transformed with a vector containing heterologous DNA. Host cells serve two purposes by providing the cellular machinery to replicate the vector and/or express the protein coding regions in the vector.

Preferred host cells of the invention are *E. coli* cells containing a vector comprising a cPLA2 gene and can serve in both the cloning and expressing capacity. Because the cPLA2 gene was isolated from human cells, a more preferred host cell is a eukaryotic cell transformed by a eukaryotic expression vector comprising a cPLA2-encoding DNA sequence. More highly preferred host cells are mammalian cell lines transformed by a eukaryotic expression vector comprising a cPLA2 gene. The most preferred host cells are the human embryohal kidney cell line 293 transformed by pHDCPF or pHDCPFS and the AV12 hamster cell line transformed by pHDCPF or pHDCPFS. The most highly preferred cPLA2 host cells of the invention are the human embryonal kidney cell line 293 transformed by pHDCPFS and the AV12 hamster cell line transformed by pHDCPFS. Both non-transformed cell lines are a permanent part of the American Type Culture Collection (ATCC).

Yet another embodiment of the invention is a method of using a cPLA$_2$-encoding gene to transform a cell. There is a wide variety of tranformation techniques applicable to both prokaryotic and eukaryotic cells which will not be discussed, because such transformation methods are old in the art.

A further embodiment of the invention consists of a method of using a cPLA$_2$ host cell to express cPLA$_2$. In this embodiment, a host cell, either prokaryotic or eukaryotic, that has been transformed is cultured in an appropriate medium until a substantial cell mass has been obtained. Fermentation of transformed prokaryotes and mass cell culture of transformed eukaryotic cells is old in the art and will not be discussed for that reason.

The second step of this embodiment is the isolation of cPLA$_2$ from the cultured cells. Two methods for purifying cPLA$_2$ from a non-transformed mammalian cell line are described in U.S. patent application Ser. No. 07/573,513. The following summarizes those methods.

Once grown and harvested, the cultured cells are lysed by nitrogen cavitation in the presence of protease inhibitors. A soluble fraction is prepared from the lysate by ultracentrifugation. The resulting solution of cytosolic proteins contains cPLA$_2$ and is subjected to a series of purification procedures.

The soluble fraction of the cell lysate is run through a series of column chromatography procedures. Anion exchange chromatography is followed by hydrophobic interaction, molecular sizing and finally another hydrophobic interaction technique where the conditions are such that the cPLA$_2$ binds the resin weakly. Each column is run individually, and the eluate is collected in fractions while monitoring for absorbance at 280 nm. Fractions are assayed for phospholipase A$_2$ activity, and those fractions with the desired activity are then run over the next column until a homogeneous solution of cPLA$_2$ is obtained.

Immunoaffinity purification using anti-cPLA$_2$ antibodies is an alternative to the series of chromatographic procedures already mentioned. Making antiserum or monoclonal antibodies directed against a purified protein is well known in the art, and skilled artisans readily will be able to prepare anti-cPLA$_2$ antibodies. Preparing an immunoaffinity matrix using such antibodies and isolating cPLA$_2$ using the immunoaffinity matrix is also well within the skill of the art. See *Affinity Chromatography Principles & Methods*, Pharmacia Fine Chemicals, 1983.

The invention also encompasses a method of using a cPLA$_2$-encoding gene to screen compounds. By using purified, recombinantly or even naturally produced cPLA$_2$, it is possible to test whether a particular compound is able to inhibit or block cPLA$_2$ enzyme activity. By adding the test compound over a wide range of concentrations to the substrate solution described in Example 1 below, it is trivial to determine whether a given compound is able to inhibit or block the enzyme's activity.

The following examples will help describe how the invention is practiced and will illustrate the characteristics of the claimed cPLA$_2$-encoding genes, vectors, host cells, and methods of the invention.

EXAMPLE 1 cPLA$_2$ Enzymatic Activity Assay

The substrate, sonicated liposomes containing 1-palmitoyl-2-[$^{14}$C]arachidonoyl-sn-glyceo-3-phosphocholine ([$^{14}$C]PC, 55 mCi/mmol from NEN Research Products) and sn-1,2-dioleoylglycerol (DG, Avanti Polar Lipids, Birmingham, Ala.) at a molar ratio of 2:1, was prepared as follows. [$^{14}$C]PC (20 nmol, $1 \times 10^6$ dpm, 50 uCi/ml in toluene/ethanol) and DG (10 nmol, 100 ug/ml in chloroform) were dried under nitrogen. The lipids were dispersed in 1 ml of 150 mM NaCl, 50 mM Hepes, pH 7.5 (assay buffer) by sonication at 4° C., with a Microson probe-sonicator (Heat Systems Ultrasonics) for $4 \times 15$ seconds, with 45 second intervals. Bovine serum albumin (essentially fatty acid free, from a 100 mg/ml stock in water, Sigma) was added to a final concentration of 4 mg/ml. Samples to be assayed for cPLA$_2$ activity were incubated with 50 ul liposomes (0.5 nmol [$^{14}$C]PC, 50,000 dpm containing 0.25 nmol of DG) in a total volume of 0.2 ml of assay buffer containing 1 mM CaCl$_2$ and 1 mM 2-ME. Incubations were carried out at 37° C. for 15 minutes and terminated by adding 2 ml of Dole's reagent (2-propanol/heptane/0.5M sulfuric acid, 40:10:1 containing 10 ug/ml of stearic acid). After mixing, 1.2 ml of heptane and 1 ml of water were added. The mixtures were briefly vortexed and the upper phase transferred to tubes containing 2 ml of heptane and 150 mg of Bio-Sil (Bio-Rad Laboratories) activated at 130° C. before use. The tubes were thoroughly vortexed and centrifuged (1000×g for 5 minutes). The supernatants were decanted into scintillation vials. After addition of 10 ml of a liquid scintillation cocktail (Ready Protein+, Beckman) radioactivity was counted using a Beckman liquid scintillation counter Model LS 7000. High radioactive counts correlate with enzymatic activity.

EXAMPLE 2

Prokaryotic Expression of $cPLA_2$

E. coli K12 DH5 alpha/pECPLA21 and E. Coli K12×E. coli B hybrid RR1/pECPLA22 were deposited at the Northern Regional Research Laboratories (NRRL) under accession numbers NRRL B-18774 and NRRL B-18775 respectively. The deposits were made in accordance with the terms of the Budapest Treaty. Both strains carried closed circular plasmids that contain $cPLA_2$-encoding cDNA, a tetracycline resistance-conferring gene, the temperature sensitive cI857 repressor that regulates the lambda pL promoter and other regulatory elements necessary for transcription and translation in E. coli.

E. coli K12×E. coli B hybrid RR1/pECPLA22 was grown overnight in Tryptone broth supplemented with 10 ug/ml tetracycline (TY) at 28° C., then diluted 1:10 with the TY broth and agitated for 60 minutes at 28° C. After the initial growth phase, the cells were induced by raising the culture temperature to 42° C. for six hours. The induced cells were lysed by treatment with a 1 mg/ml (final concentration in water) lysozyme solution and sonicated six times for 15 seconds, at 45 second intervals. A transformed and a non-transformed cell lysate were prepared and assayed for protein content. The samples were then assayed for $cPLA_2$ activity according to Example 1.

Figure 4:
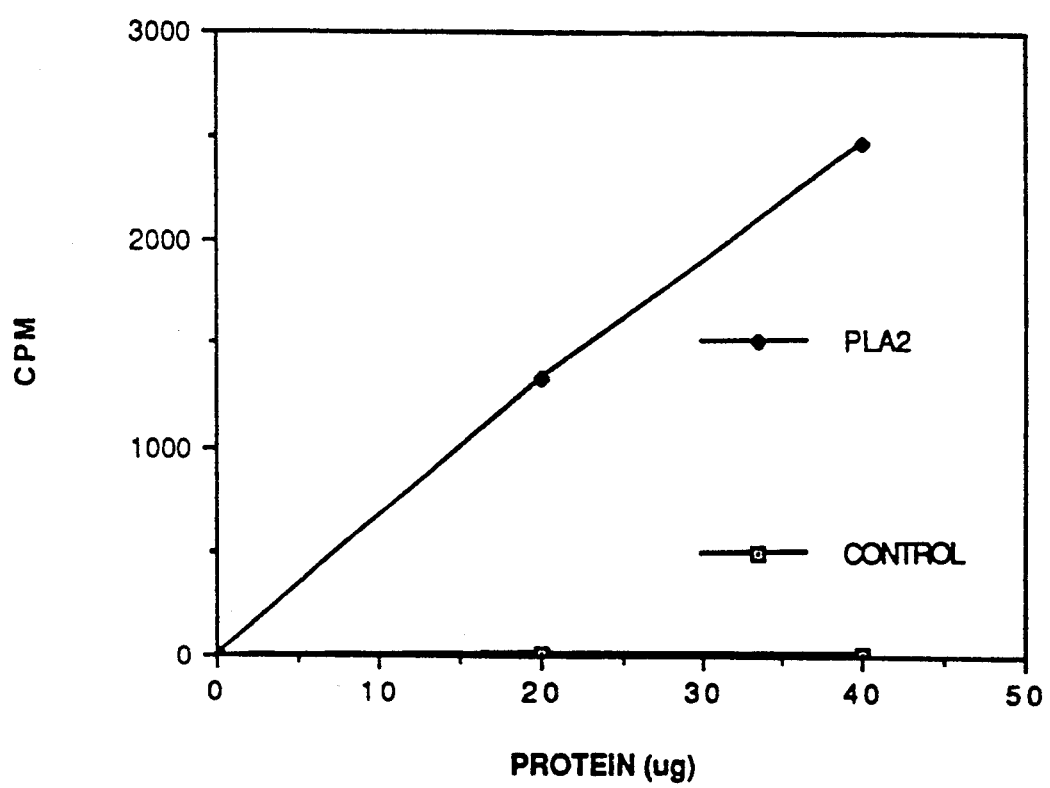
FIG. 4 shows the enzymatic activity versus protein content found in transformed and non-transformed *E. coli* cells. The data unmistakably illustrates that the *E. coli* cells which were transformed with one of the vectors of the invention express significantly more cPLA₂ than the control cells.

FIG. 4 shows the enzymatic activity found in each sample versus its protein content. E. coli cells that did not contain $cPLA_2$-encoding DNA were used as the negative control. The data unmistakably illustrated that the E. coli cells which were transformed with one of the vectors of the invention expressed significantly more $cPLA_2$ than did the control cells.

EXAMPLE 3

Eukaryotic Expression of $cPLA_2$

Transient expression of $cPLA_2$ was achieved in the human embryonal kidney cell line 293. The line is a permanent part of the American Type Culture Collection (ATCC) and is available under accession number CRL 1573.

E. coli K12 DH5 alpha/pHDCPF and E. coli K12 DH5 alpha/pHDCPFS were deposited at the Northern Regional Research Laboratories (NRRL) under accession numbers NRRL B-18772 and NRRL B-18773 respectively. The deposits were made in accordance with the terms of the Budapest Treaty. Both strains carried closed circular plasmids containing $cPLA_2$-encoding cDNA, ampicillin and hygromycin resistance-conferring genes, the dihydrofolate reductase gene, the adenovirus major late promoter and other regulatory elements necessary for transcription and translation in eukaryotic cells.

A) Plasmid Isolation

One half liter of DS broth (12 gm tryptone, 24 gm yeast extract, 4 ml glycerol, 100 ml of 0.17M $KH_2PO_4+0.72M$ $K_2HPO_4$ per liter) containing 100 ug/ml ampicillin was inoculated with E. coli K12 DH5 alpha/pHDCPFS cells and incubated in an air shaker at 37° C. overnight.

The culture was then removed and centrifuged in a Sorvalt GSA rotor (Dupont Co., Instrument Products, Newtown, Conn. 06470) at 7500 rpm for 10 minutes at 4° C. The resulting supernatant was discarded, and the cell pellet was resuspended in 14 mls of a solution of 25% sucrose and 50 mM Tris/HCl (Sigma), pH 8.0; the mixture was then transferred to an oakridge tube. Two mls of a 10 mg/ml lysozyme solution and 0.75 ml of 0.5M ethylene diamine tetraacetic acid (EDTA) pH 8.4 were added to the solution, which was then incubated on ice for 15 minutes. 1.5 mls of Triton lytic mix (3% Triton X-100 (Sigma), 0.19M EDTA, 0.15M Tris/HCl pH 8.0) was added to the solution, which was then incubated for 15 minutes. The solution was centrifuged in a Sorvall SS34 rotor (Dupont Co., Instrument products, Newtown, Conn. 06470) at 20,000 rpm for 45 minutes at 4°. The resulting supernatant containing plasmid DNA was removed and mixed with a solution of 20.55 g CsCl, 0.28 ml of 1M Tris/HCl pH 8.0, and 1.35 mls of a 10 mg/ml ethidium bromide (EtBr) solution. The final volume of the mixture was brought to 27 mls with water. The mixture was centrifuged in two Quick-seal tubes (Beckman Cat. #342413) in a Ti 75 rotor (Beckman Instruments, Inc.) at 45,000 rpm for 4 days at 20° C. Plasmid bands were collected separately into two new Quick-seal tubes. 150 ul of EtBr (10 mg/ml) was added into each tube and then the tubes were topped off with a $CsCl/H_2O$ (double distilled, deionized water) solution (density=1.56 g/ml) and centrifuged in a Ti 75 rotor at 45,000 rpm for 24 hours at 20° C.

The plasmid band was collected and an equal volume of water was added to dilute the CsCl. EtBr was extracted 5 times with between 2 and 3 volumes of 1-butanol. 2.5 volumes of absolute ethanol was added to the extracted solution containing plasmid, which was incubated at room temperature for 5–10 minutes and then centrifuged in a Soyall SS34 rotor at 10,000 rpm for 10 minutes. The DNA pellet was dried and then dissolved in 200 ul of TE solution (1 mM EDTA, 10 mM Tris/HCl pH 8.0).

B) Transfection of Eukaryotic Cell Line 293

One day prior to transfection, 293 cells were seeded in two, 100 cm² culture dishes (Falcon #1005) at a density of 1×10⁶ cells per dish. The cells were seeded and grown in DMEM (Dulbecco's Modified Eagle Medium; GIBCO, Grand Island, N.Y.) supplemented with 10% fetal bovine serum (Hyclone; Ogden, Utah) and 50 mg/ml of gentamycin (GIBCO) in a 5% $CO_2$, humidified 37° C. incubator. Approximately 20 ugs of purified pHDCPF DNA was added to a calcium phosphate transfection buffer (see Wigler et al., P.N.A.S., 76, (1979) in the absence of any carrier DNA. The transfection was allowed to proceed for four hours at 37° C., after which the transfection buffer was replaced with DMEM, supplemented as described above, and the cells were allowed to grow for three days.

C) Cell Lysis

The transfected cultures were washed once with wash buffer (140 mM NaCl, 5 mM KCl, 2 mM EDTA, 25 mM HEPES, pH 7.4) and were removed from the culture dishes by adding 10 mls of wash buffer followed by scraping. The cells (approximately $1 \times 10^7$) were placed in a conical tube and centrifuged. One ml of wash buffer plus 1 mM phenylmethane sulfonyl fluoride, 100 uM leupeptin and 100 uM pepstatin A was added to the pellet and the cells were lysed using a probe sonicator (Model W-385, Heat Systems Ultrasonics) with a stepped microtip at an output setting of 1. Sonication was repeated six times for 15 seconds at 45 second intervals.

Figure 5:
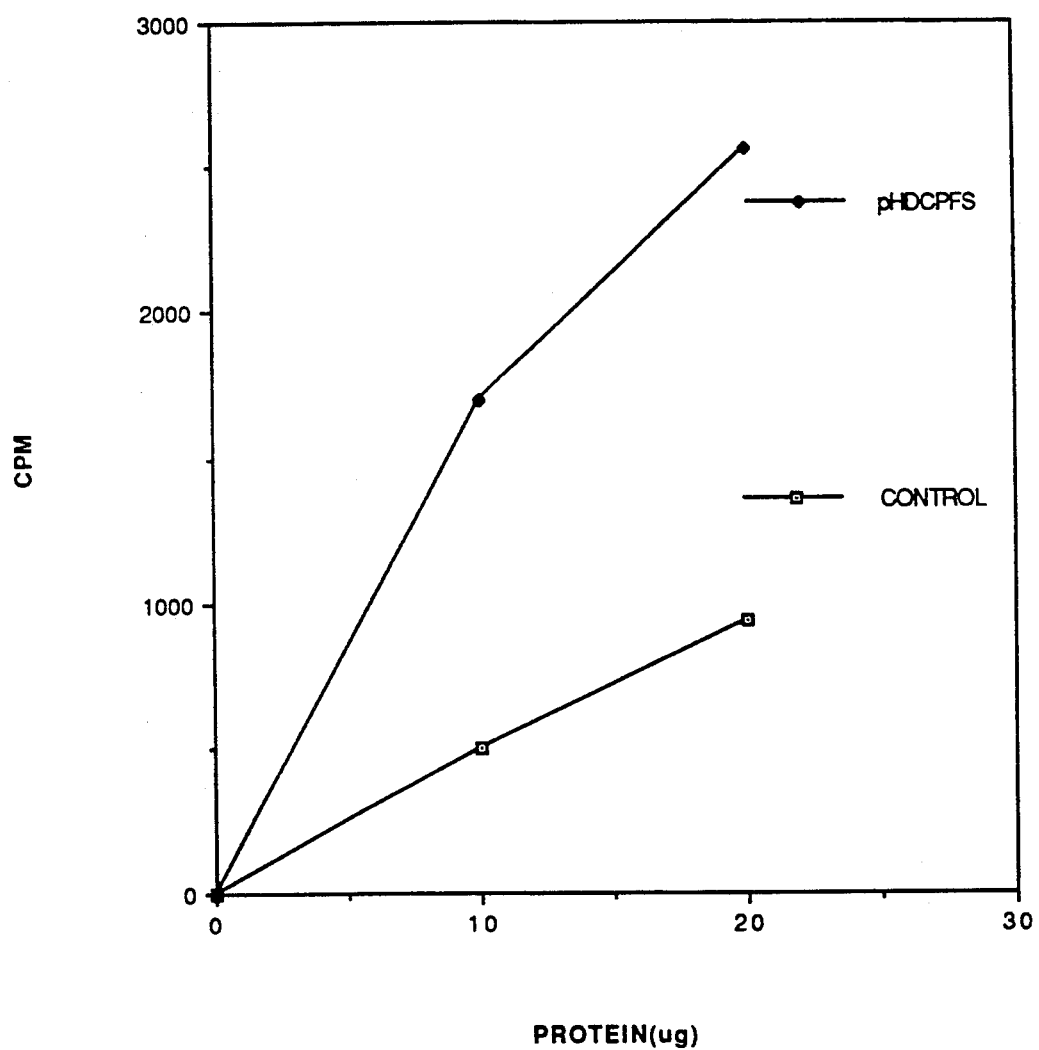
FIG. 5 shows the results of a transient expression experiment using a 293 cell culture transformed with vector pHDCPFS.

The transfected 293 lysates were then assayed for $cPLA_2$ activity according to Example 1. The results from one such lysate are shown in FIG. 5 where $cPLA_2$ activity is plotted against the protein content of the lysate. Untransfected cells, otherwise handled in an identical manner, were used as the negative control. The graph clearly shows that the transfected cells had higher $cPLA_2$ activity than did the negative control. The increased enzymatic activity demonstrates that plasmid pHDCPFS was able to successfully express $cPLA_2$.

EXAMPLE 4

Stable Eukaryotic Expression of $cPLA_2$

Stable expression of $cPLA_2$ was achieved in the human embryohal kidney cell line 293 and in the AV12 hamster cell line. The AV12 cell line is a permanent part of the ATCC and is available under accession number CRL9595, and the 293 cell line is a permanent part of the ATCC and is available under accession number CRL1573. Plasmids containing the $cPLA_2$-encoding gene were prepared according to Example 3 A).

Both mammalian cell lines were transfected with pHDCPFS according to Example 3B) except that the plasmid DNA was first linearized by digestion with restriction enzyme Fsp I and precipitated with ethanol. After transfection, both cell lines were individually seeded into culture plates and grown for three days in DMEM after which the medium was replaced with selective medium (DMEM supplemented as described above plus 200 ug/ml hygromycin) to kill any cells which did not take up the linearized plasmid DNA.

After 5 days, most of the originally seeded cells had spontaneously detached from the culture plates and were removed by the weekly changes of medium (twice weekly for AV12 cells); however, colonies grew from both cell lines. These colonies were transferred to 24-well trays (Costar Inc.) using plastic pipet tips.

Figure 6:
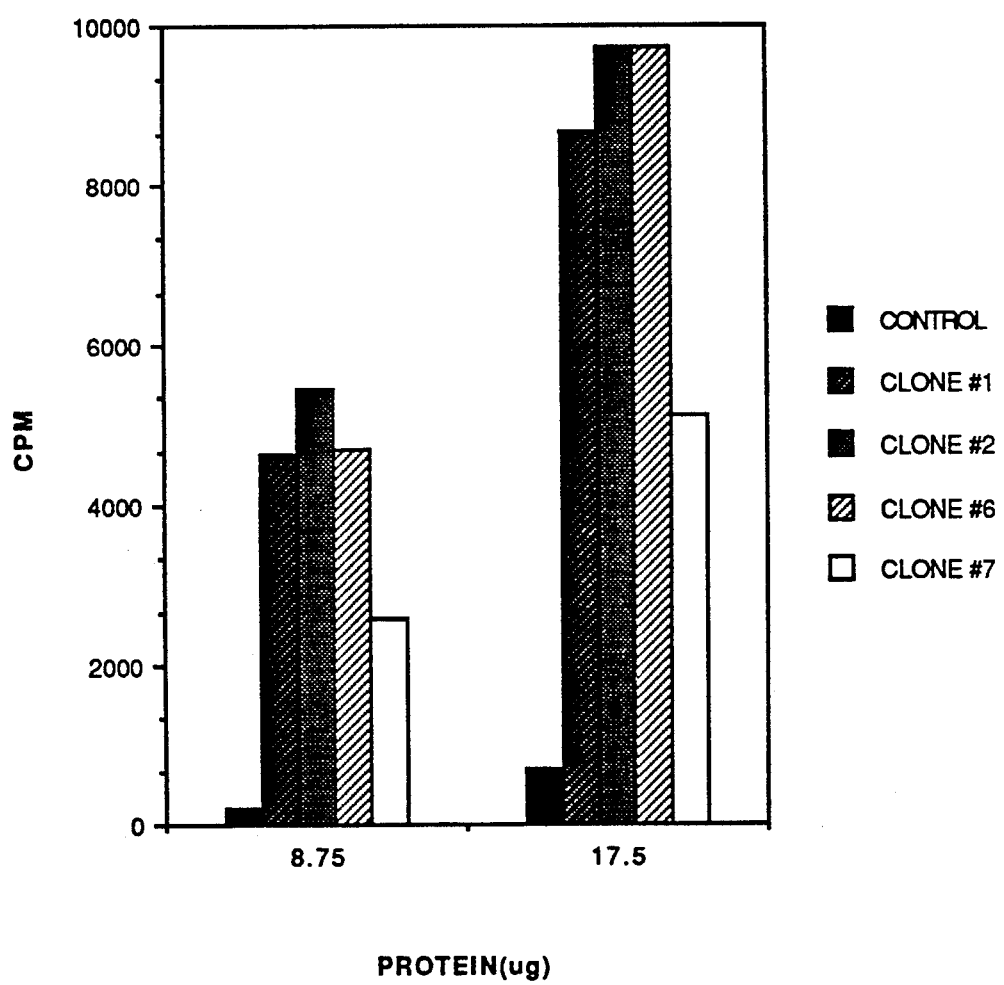
FIGS. 6 and 7 show the cPLA₂ activity of pHDCPFS transformed AV12 hamster cell lines.
Figure 7:
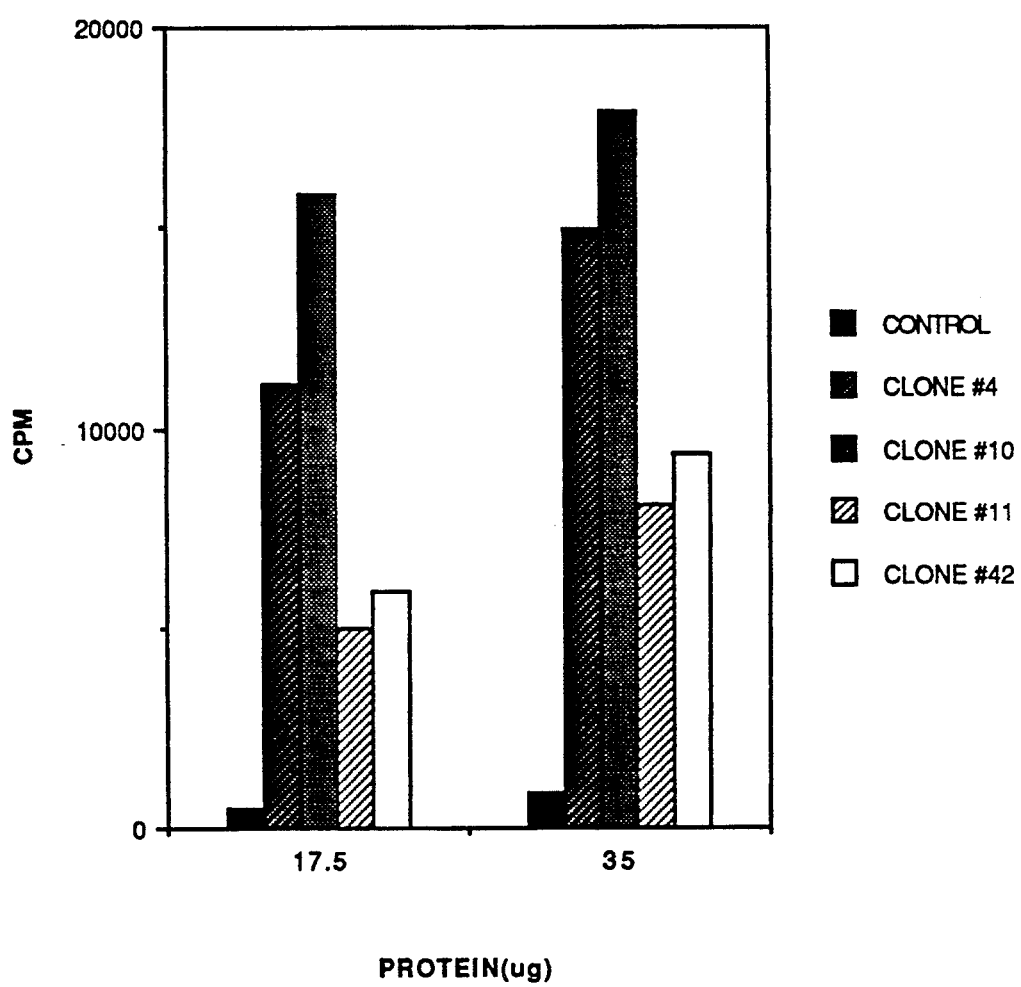
Figure 8:
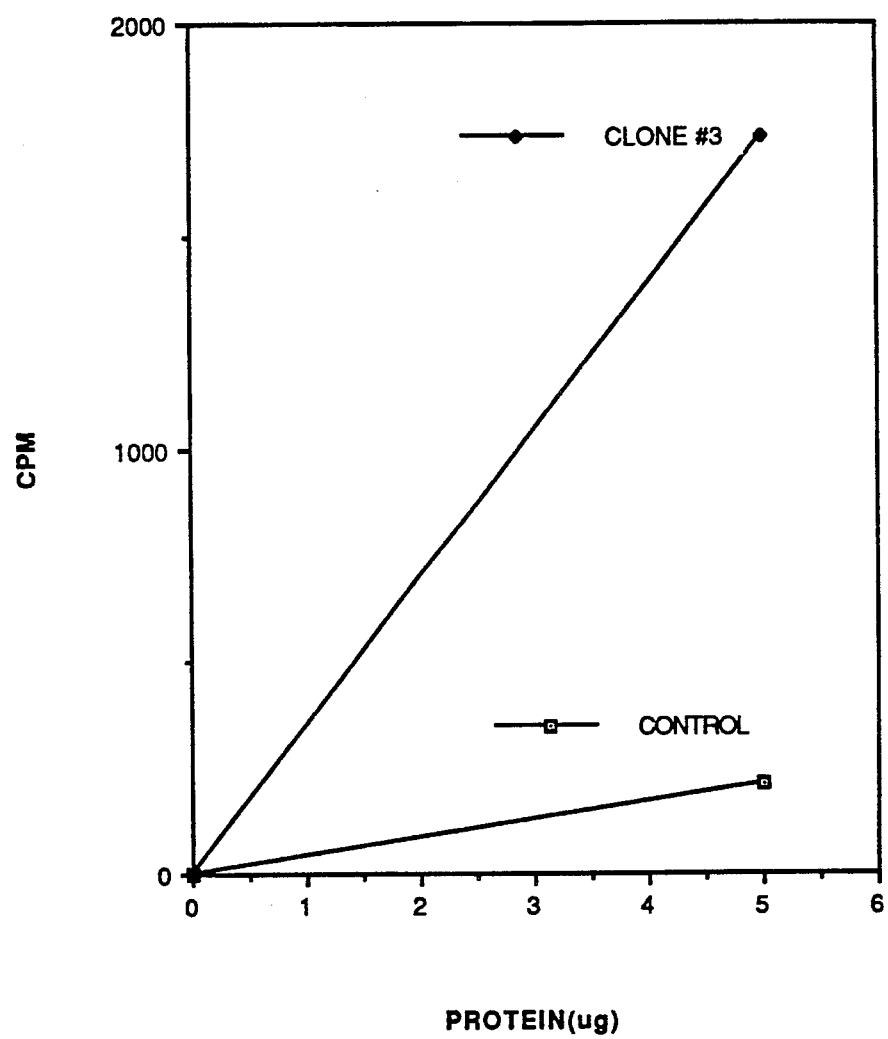
FIG. 8 shows the cPLA₂ activity of a pHDCPFS transformed 293 human kidney cell line.

The transfected lines were grown and assayed as described in Examples 1 and 3, and the results are shown in FIGS. 6–8. FIGS. 6 and 7 show the results of eight transformed AV12 cell lines and FIG. 8 shows the results of one transformed 293 cell line. The negative controls were the non-transformed cell lines handled in the same fashion. The results clearly show that stable cell lines expressing $cPLA_2$ were obtained by transformation with vectors of the invention. To date, lorry-eight transformed AV12 and six transformed 293 cell lines have been assayed, and all expressed $cPLA_2$ above control levels.

EXAMPLE 5

Western Blot Analysis

Immunological and electrophoretic equivalence between naturally-occurring $cPLA_2$, described in U.S. patent application Ser. No. 07/573,513, and recombinant $cPLA_2$ produced using one of the DNA sequences of the present invention, was established by western blot analysis. The samples and the procedure used are described below.

Sample 1

E. coli K12×E. coli B hybrid RR1/pECPLA22 cells, described in Example 2, were grown to an $O.D._{600}$ of 1.0. One ml of cells was centrifuged, and the medium was removed. The pellet was dissolved in 250 uls of loading buffer (0.125M Tris/HCl, pH 6.8 containing 2% SDS, 30% glycerol, 0.1% Bromophenol Blue (Sigma), 6M urea, and 10% 2-mercaptoethanol).

Sample 2

E. coli K12×E. coli B hybrid RR1 cells which did not contain the $cPLA_2$-encoding plasmid pECPLA22 were grown and handled as stated in Sample 1.

Sample 3

500 ngs of naturally-occurring $cPLA_2$ isolated from the human monoblastoid cell line U937 as described in U.S. patent application Ser. No. 07/573,513 were mixed with 30 uls of loading buffer.

All samples were heated at 100° C. for five minutes, and 30 uls of each were loaded onto separate lanes of a 10% SDS polyacrylamide gel (160×140×1.5 mm). The gel was run at 50 mA until the dye reached the bottom of the gel. The proteins were transferred to a ProBlott ™ membrane (Applied Biosystems) using a BioRad Transblot apparatus run in 20 mM CAPS buffer, pH 11 (Sigma, C-2632) at 250 mA for 2 hours. After the proteins were transferred, the filter was removed and washed 3 times for 5 minutes at room temperature in TBST (0.15M NaCl, 0.1% Tween 20, 50 mM Tris/HCl, pH 8.0) on a rocking platform. The blot was then blocked for 3 hours in TBS (0.15M NaCl, 50 mM Tris/HCl, pH 8.0) containing 5% non-fat dried milk (Carnation), then blocked again for 3 hours in TBS+3% bovine serum albumin. The blot was then washed 3 times for 5 minutes in 100 mls of TBST.

Monoclonal antibodies specific for $cPLA_2$ were described in U.S. patent application Ser. No. 07/663,335. One of those antibodies (3.1) was used as the primary antibody to probe the blot for $cPLA_2$ in the present example. The primary antibody, at a concentration of 0.5 mg/ml, was diluted 1:570 in TBST plus 0.02% sodium azide. The protein-containing blot was incubated overnight at 4° C. in the primary antibody solution and then washed as before.

The blot was then reacted with a secondary antibody by incubating it for 6 hours at room temperature in a solution of immunoaffinity purified rabbit anti-mouse IgG antibody (Jackson ImmunoResearch, Cat. #315-005-045) diluted 1:5000 in TBST. The blot was then washed as before, followed by incubation at 4° C. overnight in a 1:500 dilution (TBST) of goat anti-rabbit IgG conjugated to horseradish peroxidase (Pel-freeze, Cat. #721307-1). The blot was washed as before and developed for 60 minutes at room temperature in a solution of 42 mls of 0.1M phosphate buffer, pH 6; 8 mls of 4-chloronapthol (3 mg/ml in methanol) containing 300 uls of 3% hydrogen peroxide.

Figure 9:
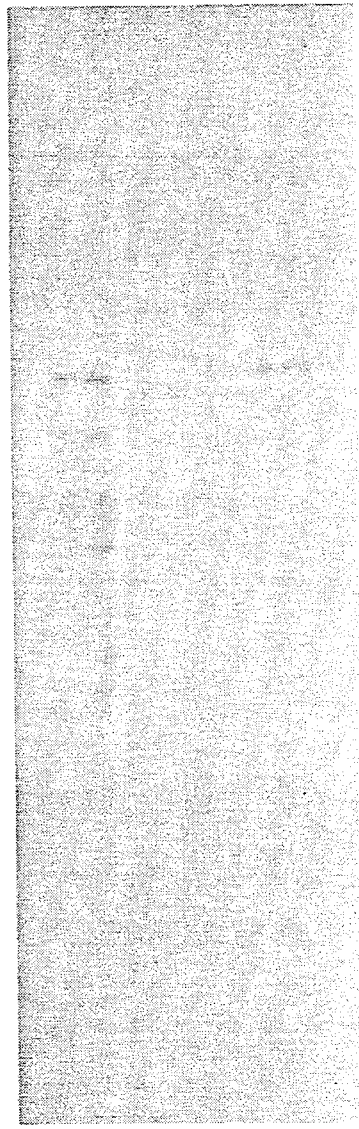
FIG. 9 represents an immunoblot comparing cPLA₂ expression in a pECPLA22 transformed *E. coli* culture (lane 1) with a non-transformed *E. coli* culture (lane 2) and naturally-occurring cPLA₂ isolated from a human monoblastoid cell line (lane 3).

The results of the western blot analysis are shown in FIG. 9. The stained bands in Samples 1 and 3 demonstrate that the naturally-occuring cPLA$_2$ found in the U937 cell line has the same mobility when run on an SDS gel as the recombinantly produced cPLA$_2$ encoded by one of the claimed DNA sequences of the invention. Sample 2, the negative control, shows that without a vector of the invention, cPLA$_2$ is not expressed.

---

We claim:

1. A gene consisting essentially of a recombinant DNA sequence that encodes a protein having the amino acid sequence of SEQ ID NO:2.

2. The gene of claim 1 wherein said encoded protein has cytosolic phospholipase A₂ (cPLA₂) activity of greater than 6 micromoles per minute per milligram, an apparent molecular weight of approximately 100,000 daltons as determined by sodium dodecyl sulphate polyacrylamide gel electrophoresis, and is activated over the range of from 150 to 600 nM Ca++.

3. The gene of claim 2 wherein said DNA sequence is the DNA sequence of SEQ ID NO:1.

4. A recombinant DNA vector comprising a gene of claim 1.

5. A recombinant DNA vector comprising the gene of claim 3.

6. The vector of claim 5 selected from the group consisting of pECPLA22, pHDCPF, and pHDCPFS.

7. A recombinant host cell comprising the vector of claim 4.

8. The vector of claim 6 that is plasmid pECPLA22.

9. A recombinant host cell comprising the vector of claim 8.

10. The host cell of claim 9 that is E. coli K12×E. coli B hybrid RR1/pECPLA22 which is on deposit with the NRRL under accession number 18775.

11. The vector of claim 6 wherein the vector is a eukaryotic expression vector selected from the group consisting of pHDCPF and pHDCPFS.

12. The vector of claim 11 that is plasmid pHDCPF.

13. A recombinant host cell comprising the vector of claim 11.

14. The host cell of claim 13 that is E. coli K12 DH5 alpha/pHDCPF and is on deposit with the NRRL under accession number 18772.

15. The vector of claim 11 that is plasmid pHDCPFS.

16. A recombinant host cell comprising the vector of claim 15.

17. The host cell of claim 16 that is E. coli K12 DH5 alpha/pHDCPFS and is on deposit with the NRRL under accession number 18773.

18. A host cell comprising a eukaryotic cell transformed with the vector of claim 4.

19. A host cell comprising a eukaryotic cell transformed with the vector of claim 5.

20. The host cell of claim 19 wherein the cell is the human embryonal kidney cell line 293 and the vector is pHDCPF or pHDCPFS.

21. The host cell of claim 19 wherein the cell is the hamster cell line AV12 and the vector is pHDCPF or pHDCPFS.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 2247 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..2247

( x i ) SEQUENCE DESCRIPTION: SEQ ID NO:1:

```
ATG TCA TTT ATA GAT CCT TAC CAG CAC ATT ATA GTG GAG CAC CAG TAT         48
Met Ser Phe Ile Asp Pro Tyr Gln His Ile Ile Val Glu His Gln Tyr
 1               5                  10                  15

TCC CAC AAG TTT ACG GTA GTG GTG TTA CGT GCC ACC AAA GTG ACA AAG         96
Ser His Lys Phe Thr Val Val Val Leu Arg Ala Thr Lys Val Thr Lys
                20                  25                  30

GGG GCC TTT GGT GAC ATG CTT GAT ACT CCA GAT CCC TAT GTG GAA CTT        144
Gly Ala Phe Gly Asp Met Leu Asp Thr Pro Asp Pro Tyr Val Glu Leu
                35                  40                  45

TTT ATC TCT ACA ACC CCT GAC AGC AGG AAG AGA ACA AGA CAT TTC AAT        192
Phe Ile Ser Thr Thr Pro Asp Ser Arg Lys Arg Thr Arg His Phe Asn
        50                  55                  60

AAT GAC ATA AAC CCT GTG TGG AAT GAG ACC TTT GAA TTT ATT TTG GAT        240
Asn Asp Ile Asn Pro Val Trp Asn Glu Thr Phe Glu Phe Ile Leu Asp
 65                  70                  75                  80

CCT AAT CAG GAA AAT GTT TTG GAG ATT ACG TTA ATG GAT GCC AAT TAT        288
Pro Asn Gln Glu Asn Val Leu Glu Ile Thr Leu Met Asp Ala Asn Tyr
                85                  90                  95

GTC ATG GAT GAA ACT CTA GGG ACA GCA ACA TTT ACT GTA TCT TCT ATG        336
Val Met Asp Glu Thr Leu Gly Thr Ala Thr Phe Thr Val Ser Ser Met
                100                 105                 110

AAG GTG GGA GAA AAG AAA GAA GTT CCT TTT ATT TTC AAC CAA GTC ACT        384
Lys Val Gly Glu Lys Lys Glu Val Pro Phe Ile Phe Asn Gln Val Thr
            115                 120                 125

GAA ATG GTT CTA GAA ATG TCT CTT GAA GTT TGC TCA TGC CCA GAC CTA        432
Glu Met Val Leu Glu Met Ser Leu Glu Val Cys Ser Cys Pro Asp Leu
        130                 135                 140

CGA TTT AGT ATG GCT CTG TGT GAT CAG GAG AAG ACT TTC AGA CAA CAG        480
Arg Phe Ser Met Ala Leu Cys Asp Gln Glu Lys Thr Phe Arg Gln Gln
145                 150                 155                 160

AGA AAA GAA CAC ATA AGG GAG AGC ATG AAG AAA CTC TTG GGT CCA AAG        528
Arg Lys Glu His Ile Arg Glu Ser Met Lys Lys Leu Leu Gly Pro Lys
                165                 170                 175

AAT AGT GAA GGA TTG CAT TCT GCA CGT GAT GTG CCT GTG GTA GCC ATA        576
Asn Ser Glu Gly Leu His Ser Ala Arg Asp Val Pro Val Val Ala Ile
                180                 185                 190

TTG GGT TCA GGT GGG GGT TTC CGA GCC ATG GTG GGA TTC TCT GGT GTG        624
Leu Gly Ser Gly Gly Gly Phe Arg Ala Met Val Gly Phe Ser Gly Val
                195                 200                 205

ATG AAG GCA TTA TAC GAA TCA GGA ATT CTG GAT TGT GCT ACC TAC GTT        672
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Met | Lys | Ala | Leu | Tyr | Glu | Ser | Gly | Ile | Leu | Asp | Cys | Ala | Thr | Tyr | Val |      |
|     | 210 |     |     |     | 215 |     |     |     |     | 220 |     |     |     |     |     |      |
| GCT | GGT | CTT | TCT | GGC | TCC | ACC | TGG | TAT | ATG | TCA | ACC | TTG | TAT | TCT | CAC | 720  |
| Ala | Gly | Leu | Ser | Gly | Ser | Thr | Trp | Tyr | Met | Ser | Thr | Leu | Tyr | Ser | His |      |
| 225 |     |     |     |     | 230 |     |     |     |     | 235 |     |     |     |     | 240 |      |
| CCT | GAT | TTT | CCA | GAG | AAA | GGG | CCA | GAG | GAG | ATT | AAT | GAA | GAA | CTA | ATG | 768  |
| Pro | Asp | Phe | Pro | Glu | Lys | Gly | Pro | Glu | Glu | Ile | Asn | Glu | Glu | Leu | Met |      |
|     |     |     |     |     | 245 |     |     |     | 250 |     |     |     |     | 255 |     |      |
| AAA | AAT | GTT | AGC | CAC | AAT | CCC | CTT | TTA | CTT | CTC | ACA | CCA | CAG | AAA | GTT | 816  |
| Lys | Asn | Val | Ser | His | Asn | Pro | Leu | Leu | Leu | Leu | Thr | Pro | Gln | Lys | Val |      |
|     |     |     | 260 |     |     |     |     | 265 |     |     |     |     | 270 |     |     |      |
| AAA | AGA | TAT | GTT | GAG | TCT | TTA | TGG | AAG | AAG | AAA | AGC | TCT | GGA | CAA | CCT | 864  |
| Lys | Arg | Tyr | Val | Glu | Ser | Leu | Trp | Lys | Lys | Lys | Ser | Ser | Gly | Gln | Pro |      |
|     |     | 275 |     |     |     |     | 280 |     |     |     |     | 285 |     |     |     |      |
| GTC | ACC | TTT | ACT | GAC | ATC | TTT | GGG | ATG | TTA | ATA | GGA | GAA | ACA | CTA | ATT | 912  |
| Val | Thr | Phe | Thr | Asp | Ile | Phe | Gly | Met | Leu | Ile | Gly | Glu | Thr | Leu | Ile |      |
|     | 290 |     |     |     |     | 295 |     |     |     |     | 300 |     |     |     |     |      |
| CAT | AAT | AGA | ATG | AAT | ACT | ACT | CTG | AGC | AGT | TTG | AAG | GAA | AAA | GTT | AAT | 960  |
| His | Asn | Arg | Met | Asn | Thr | Thr | Leu | Ser | Ser | Leu | Lys | Glu | Lys | Val | Asn |      |
| 305 |     |     |     |     | 310 |     |     |     |     | 315 |     |     |     |     | 320 |      |
| ACT | GCA | CAA | TGC | CCT | TTA | CCT | CTT | TTC | ACC | TGT | CTT | CAT | GTC | AAA | CCT | 1008 |
| Thr | Ala | Gln | Cys | Pro | Leu | Pro | Leu | Phe | Thr | Cys | Leu | His | Val | Lys | Pro |      |
|     |     |     |     | 325 |     |     |     |     | 330 |     |     |     |     | 335 |     |      |
| GAC | GTT | TCA | GAG | CTG | ATG | TTT | GCA | GAT | TGG | GTT | GAA | TTT | AGT | CCA | TAC | 1056 |
| Asp | Val | Ser | Glu | Leu | Met | Phe | Ala | Asp | Trp | Val | Glu | Phe | Ser | Pro | Tyr |      |
|     |     |     | 340 |     |     |     |     | 345 |     |     |     |     | 350 |     |     |      |
| GAA | ATT | GGC | ATG | GCT | AAA | TAT | GGT | ACT | TTT | ATG | GCT | CCC | GAC | TTA | TTT | 1104 |
| Glu | Ile | Gly | Met | Ala | Lys | Tyr | Gly | Thr | Phe | Met | Ala | Pro | Asp | Leu | Phe |      |
|     |     | 355 |     |     |     |     | 360 |     |     |     |     | 365 |     |     |     |      |
| GGA | AGC | AAA | TTT | TTT | ATG | GGA | ACA | GTC | GTT | AAG | AAG | TAT | GAA | GAA | AAC | 1152 |
| Gly | Ser | Lys | Phe | Phe | Met | Gly | Thr | Val | Val | Lys | Lys | Tyr | Glu | Glu | Asn |      |
|     | 370 |     |     |     |     | 375 |     |     |     |     | 380 |     |     |     |     |      |
| CCC | TTG | CAT | TTC | TTA | ATG | GGT | GTC | TGG | GGC | AGT | GCC | TTT | TCC | ATA | TTG | 1200 |
| Pro | Leu | His | Phe | Leu | Met | Gly | Val | Trp | Gly | Ser | Ala | Phe | Ser | Ile | Leu |      |
| 385 |     |     |     |     | 390 |     |     |     |     | 395 |     |     |     |     | 400 |      |
| TTC | AAC | AGA | GTT | TTG | GGC | GTT | TCT | GGT | TCA | CAA | AGC | AGA | GGC | TCC | ACA | 1248 |
| Phe | Asn | Arg | Val | Leu | Gly | Val | Ser | Gly | Ser | Gln | Ser | Arg | Gly | Ser | Thr |      |
|     |     |     |     | 405 |     |     |     |     | 410 |     |     |     |     | 415 |     |      |
| ATG | GAG | GAA | GAA | TTA | GAA | AAT | ATT | ACC | ACA | AAG | CAT | ATT | GTG | AGT | AAT | 1296 |
| Met | Glu | Glu | Glu | Leu | Glu | Asn | Ile | Thr | Thr | Lys | His | Ile | Val | Ser | Asn |      |
|     |     |     | 420 |     |     |     |     | 425 |     |     |     |     | 430 |     |     |      |
| GAT | AGC | TCG | GAC | AGT | GAT | GAT | GAA | TCA | CAC | GAA | CCC | AAA | GGC | ACT | GAA | 1344 |
| Asp | Ser | Ser | Asp | Ser | Asp | Asp | Glu | Ser | His | Glu | Pro | Lys | Gly | Thr | Glu |      |
|     |     | 435 |     |     |     |     | 440 |     |     |     |     | 445 |     |     |     |      |
| AAT | GAA | GAT | GCT | GGA | AGT | GAC | TAT | CAA | AGT | GAT | AAT | CAA | GCA | AGT | TGG | 1392 |
| Asn | Glu | Asp | Ala | Gly | Ser | Asp | Tyr | Gln | Ser | Asp | Asn | Gln | Ala | Ser | Trp |      |
|     | 450 |     |     |     |     | 455 |     |     |     |     | 460 |     |     |     |     |      |
| ATT | CAT | CGT | ATG | ATA | ATG | GCC | TTG | GTG | AGT | GAT | TCA | GCT | TTA | TTC | AAT | 1440 |
| Ile | His | Arg | Met | Ile | Met | Ala | Leu | Val | Ser | Asp | Ser | Ala | Leu | Phe | Asn |      |
| 465 |     |     |     |     | 470 |     |     |     |     | 475 |     |     |     |     | 480 |      |
| ACC | AGA | GAA | GGA | CGT | GCT | GGG | AAG | GTA | CAC | AAC | TTC | ATG | CTG | GGC | TTG | 1488 |
| Thr | Arg | Glu | Gly | Arg | Ala | Gly | Lys | Val | His | Asn | Phe | Met | Leu | Gly | Leu |      |
|     |     |     |     | 485 |     |     |     |     | 490 |     |     |     |     | 495 |     |      |
| AAT | CTC | AAT | ACA | TCT | TAT | CCA | CTG | TCT | CCT | TTG | AGT | GAC | TTT | GCC | ACA | 1536 |
| Asn | Leu | Asn | Thr | Ser | Tyr | Pro | Leu | Ser | Pro | Leu | Ser | Asp | Phe | Ala | Thr |      |
|     |     |     | 500 |     |     |     |     | 505 |     |     |     |     | 510 |     |     |      |
| CAG | GAC | TCC | TTT | GAT | GAT | GAT | GAA | CTG | GAT | GCA | GCT | GTA | GCA | GAT | CCT | 1584 |
| Gln | Asp | Ser | Phe | Asp | Asp | Asp | Glu | Leu | Asp | Ala | Ala | Val | Ala | Asp | Pro |      |
|     |     | 515 |     |     |     |     | 520 |     |     |     |     | 525 |     |     |     |      |
| GAT | GAA | TTT | GAG | CGA | ATA | TAT | GAG | CCT | CTG | GAT | GTC | AAA | AGT | AAA | AAG | 1632 |
| Asp | Glu | Phe | Glu | Arg | Ile | Tyr | Glu | Pro | Leu | Asp | Val | Lys | Ser | Lys | Lys |      |
|     |     | 530 |     |     |     |     | 535 |     |     |     |     | 540 |     |     |     |      |

| | | | | | | | | | | | | | | | | |
|---|---|---|---|---|---|---|---|---|---|---|---|---|---|---|---|---|
| ATT | CAT | GTA | GTG | GAC | AGT | GGG | CTC | ACA | TTT | AAC | CTG | CCG | TAT | CCC | TTG | 1680 |
| Ile | His | Val | Val | Asp | Ser | Gly | Leu | Thr | Phe | Asn | Leu | Pro | Tyr | Pro | Leu | |
| 545 | | | | | 550 | | | | | 555 | | | | | 560 | |
| ATA | CTG | AGA | CCT | CAG | AGA | GGG | GTT | GAT | CTC | ATA | ATC | TCC | TTT | GAC | TTT | 1728 |
| Ile | Leu | Arg | Pro | Gln | Arg | Gly | Val | Asp | Leu | Ile | Ile | Ser | Phe | Asp | Phe | |
| | | | | 565 | | | | | 570 | | | | | 575 | | |
| TCT | GCA | AGG | CCA | AGT | GAC | TCT | AGT | CCT | CCG | TTC | AAG | GAA | CTT | CTA | CTT | 1776 |
| Ser | Ala | Arg | Pro | Ser | Asp | Ser | Ser | Pro | Pro | Phe | Lys | Glu | Leu | Leu | Leu | |
| | | | 580 | | | | | 585 | | | | | 590 | | | |
| GCA | GAA | AAG | TGG | GCT | AAA | ATG | AAC | AAG | CTC | CCC | TTT | CCA | AAG | ATT | GAT | 1824 |
| Ala | Glu | Lys | Trp | Ala | Lys | Met | Asn | Lys | Leu | Pro | Phe | Pro | Lys | Ile | Asp | |
| | | 595 | | | | | 600 | | | | | 605 | | | | |
| CCT | TAT | GTG | TTT | GAT | CGG | GAA | GGG | CTG | AAG | GAG | TGC | TAT | GTC | TTT | AAA | 1872 |
| Pro | Tyr | Val | Phe | Asp | Arg | Glu | Gly | Leu | Lys | Glu | Cys | Tyr | Val | Phe | Lys | |
| | 610 | | | | | 615 | | | | | 620 | | | | | |
| CCC | AAG | AAT | CCT | GAT | ATG | GAG | AAA | GAT | TGC | CCA | ACC | ATC | ATC | CAC | TTT | 1920 |
| Pro | Lys | Asn | Pro | Asp | Met | Glu | Lys | Asp | Cys | Pro | Thr | Ile | Ile | His | Phe | |
| 625 | | | | | 630 | | | | | 635 | | | | | 640 | |
| GTT | CTG | GCC | AAC | ATC | AAC | TTC | AGA | AAG | TAC | AAG | GCT | CCA | GGT | GTT | CCA | 1968 |
| Val | Leu | Ala | Asn | Ile | Asn | Phe | Arg | Lys | Tyr | Lys | Ala | Pro | Gly | Val | Pro | |
| | | | | 645 | | | | | 650 | | | | | 655 | | |
| AGG | GAA | ACT | GAG | GAA | GAG | AAA | GAA | ATC | GCT | GAC | TTT | GAT | ATT | TTT | GAT | 2016 |
| Arg | Glu | Thr | Glu | Glu | Glu | Lys | Glu | Ile | Ala | Asp | Phe | Asp | Ile | Phe | Asp | |
| | | | 660 | | | | | 665 | | | | | 670 | | | |
| GAC | CCA | GAA | TCA | CCA | TTT | TCA | ACC | TTC | AAT | TTT | CAA | TAT | CCA | AAT | CAA | 2064 |
| Asp | Pro | Glu | Ser | Pro | Phe | Ser | Thr | Phe | Asn | Phe | Gln | Tyr | Pro | Asn | Gln | |
| | | 675 | | | | | 680 | | | | | 685 | | | | |
| GCA | TTC | AAA | AGA | CTA | CAT | GAT | CTT | ATG | CAC | TTC | AAT | ACT | CTG | AAC | AAC | 2112 |
| Ala | Phe | Lys | Arg | Leu | His | Asp | Leu | Met | His | Phe | Asn | Thr | Leu | Asn | Asn | |
| | 690 | | | | | 695 | | | | | 700 | | | | | |
| ATT | GAT | GTG | ATA | AAA | GAA | GCC | ATG | GTT | GAA | AGC | ATT | GAA | TAT | AGA | AGA | 2160 |
| Ile | Asp | Val | Ile | Lys | Glu | Ala | Met | Val | Glu | Ser | Ile | Glu | Tyr | Arg | Arg | |
| 705 | | | | | 710 | | | | | 715 | | | | | 720 | |
| CAG | AAT | CCA | TCT | CGT | TGC | TCT | GTT | TCC | CTT | AGT | AAT | GTT | GAG | GCA | AGA | 2208 |
| Gln | Asn | Pro | Ser | Arg | Cys | Ser | Val | Ser | Leu | Ser | Asn | Val | Glu | Ala | Arg | |
| | | | | 725 | | | | | 730 | | | | | 735 | | |
| AGA | TTT | TTC | AAC | AAG | GAG | TTT | CTA | AGT | AAA | CCC | AAA | GCA | | | | 2247 |
| Arg | Phe | Phe | Asn | Lys | Glu | Phe | Leu | Ser | Lys | Pro | Lys | Ala | | | | |
| | | | 740 | | | | | 745 | | | | | | | | |

( 2 ) INFORMATION FOR SEQ ID NO:2:

( i ) SEQUENCE CHARACTERISTICS:
        ( A ) LENGTH: 749 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Ser | Phe | Ile | Asp | Pro | Tyr | Gln | His | Ile | Ile | Val | Glu | His | Gln | Tyr |
| 1 | | | | 5 | | | | | 10 | | | | | 15 | |
| Ser | His | Lys | Phe | Thr | Val | Val | Val | Leu | Arg | Ala | Thr | Lys | Val | Thr | Lys |
| | | | | 20 | | | | | 25 | | | | | 30 | |
| Gly | Ala | Phe | Gly | Asp | Met | Leu | Asp | Thr | Pro | Asp | Pro | Tyr | Val | Glu | Leu |
| | | | 35 | | | | | 40 | | | | | 45 | | |
| Phe | Ile | Ser | Thr | Thr | Pro | Asp | Ser | Arg | Lys | Arg | Thr | Arg | His | Phe | Asn |
| | | 50 | | | | | 55 | | | | | 60 | | | |
| Asn | Asp | Ile | Asn | Pro | Val | Trp | Asn | Glu | Thr | Phe | Glu | Phe | Ile | Leu | Asp |
| 65 | | | | | 70 | | | | | 75 | | | | | 80 | |
| Pro | Asn | Gln | Glu | Asn | Val | Leu | Glu | Ile | Thr | Leu | Met | Asp | Ala | Asn | Tyr |
| | | | | 85 | | | | | 90 | | | | | 95 | |

```
Val Met Asp Glu Thr Leu Gly Thr Ala Thr Phe Thr Val Ser Ser Met
            100                 105                 110

Lys Val Gly Glu Lys Lys Glu Val Pro Phe Ile Phe Asn Gln Val Thr
            115                 120                 125

Glu Met Val Leu Glu Met Ser Leu Glu Val Cys Ser Cys Pro Asp Leu
        130                 135                 140

Arg Phe Ser Met Ala Leu Cys Asp Gln Glu Lys Thr Phe Arg Gln Gln
145                     150                 155                 160

Arg Lys Glu His Ile Arg Glu Ser Met Lys Lys Leu Leu Gly Pro Lys
                165                 170                 175

Asn Ser Glu Gly Leu His Ser Ala Arg Asp Val Pro Val Val Ala Ile
            180                 185                 190

Leu Gly Ser Gly Gly Gly Phe Arg Ala Met Val Gly Phe Ser Gly Val
            195                 200                 205

Met Lys Ala Leu Tyr Glu Ser Gly Ile Leu Asp Cys Ala Thr Tyr Val
    210                 215                 220

Ala Gly Leu Ser Gly Ser Thr Trp Tyr Met Ser Thr Leu Tyr Ser His
225                 230                 235                 240

Pro Asp Phe Pro Glu Lys Gly Pro Glu Glu Ile Asn Glu Glu Leu Met
            245                 250                 255

Lys Asn Val Ser His Asn Pro Leu Leu Leu Thr Pro Gln Lys Val
            260                 265                 270

Lys Arg Tyr Val Glu Ser Leu Trp Lys Lys Lys Ser Ser Gly Gln Pro
        275                 280                 285

Val Thr Phe Thr Asp Ile Phe Gly Met Leu Ile Gly Glu Thr Leu Ile
    290                 295                 300

His Asn Arg Met Asn Thr Thr Leu Ser Ser Leu Lys Glu Lys Val Asn
305                 310                 315                 320

Thr Ala Gln Cys Pro Leu Pro Leu Phe Thr Cys Leu His Val Lys Pro
                325                 330                 335

Asp Val Ser Glu Leu Met Phe Ala Asp Trp Val Glu Phe Ser Pro Tyr
            340                 345                 350

Glu Ile Gly Met Ala Lys Tyr Gly Thr Phe Met Ala Pro Asp Leu Phe
            355                 360                 365

Gly Ser Lys Phe Phe Met Gly Thr Val Val Lys Lys Tyr Glu Glu Asn
        370                 375                 380

Pro Leu His Phe Leu Met Gly Val Trp Gly Ser Ala Phe Ser Ile Leu
385                 390                 395                 400

Phe Asn Arg Val Leu Gly Val Ser Gly Ser Gln Ser Arg Gly Ser Thr
            405                 410                 415

Met Glu Glu Glu Leu Glu Asn Ile Thr Thr Lys His Ile Val Ser Asn
            420                 425                 430

Asp Ser Ser Asp Ser Asp Asp Glu Ser His Glu Pro Lys Gly Thr Glu
        435                 440                 445

Asn Glu Asp Ala Gly Ser Asp Tyr Gln Ser Asp Asn Gln Ala Ser Trp
    450                 455                 460

Ile His Arg Met Ile Met Ala Leu Val Ser Asp Ser Ala Leu Phe Asn
465                 470                 475                 480

Thr Arg Glu Gly Arg Ala Gly Lys Val His Asn Phe Met Leu Gly Leu
            485                 490                 495

Asn Leu Asn Thr Ser Tyr Pro Leu Ser Pro Leu Ser Asp Phe Ala Thr
            500                 505                 510

Gln Asp Ser Phe Asp Asp Asp Glu Leu Asp Ala Ala Val Ala Asp Pro
        515                 520                 525
```

| | | | | | | | | | | | | | | |
|---|---|---|---|---|---|---|---|---|---|---|---|---|---|---|
| Asp | Glu 530 | Phe | Glu | Arg | Ile | Tyr 535 | Glu | Pro | Leu | Asp | Val 540 | Lys | Ser | Lys | Lys |
| Ile 545 | His | Val | Val | Asp | Ser 550 | Gly | Leu | Thr | Phe | Asn 555 | Leu | Pro | Tyr | Pro | Leu 560 |
| Ile | Leu | Arg | Pro | Gln 565 | Arg | Gly | Val | Asp | Leu 570 | Ile | Ile | Ser | Phe | Asp 575 | Phe |
| Ser | Ala | Arg | Pro 580 | Ser | Asp | Ser | Ser | Pro 585 | Pro | Phe | Lys | Glu | Leu 590 | Leu | Leu |
| Ala | Glu | Lys 595 | Trp | Ala | Lys | Met | Asn 600 | Lys | Leu | Pro | Phe | Pro 605 | Lys | Ile | Asp |
| Pro | Tyr 610 | Val | Phe | Asp | Arg | Glu 615 | Gly | Leu | Lys | Glu | Cys 620 | Tyr | Val | Phe | Lys |
| Pro 625 | Lys | Asn | Pro | Asp | Met 630 | Glu | Lys | Asp | Cys | Pro 635 | Thr | Ile | Ile | His | Phe 640 |
| Val | Leu | Ala | Asn | Ile 645 | Asn | Phe | Arg | Lys | Tyr 650 | Lys | Ala | Pro | Gly | Val 655 | Pro |
| Arg | Glu | Thr | Glu 660 | Glu | Glu | Lys | Glu | Ile 665 | Ala | Asp | Phe | Asp | Ile 670 | Phe | Asp |
| Asp | Pro | Glu 675 | Ser | Pro | Phe | Ser | Thr 680 | Phe | Asn | Phe | Gln | Tyr 685 | Pro | Asn | Gln |
| Ala | Phe 690 | Lys | Arg | Leu | His | Asp 695 | Leu | Met | His | Phe | Asn 700 | Thr | Leu | Asn | Asn |
| Ile 705 | Asp | Val | Ile | Lys | Glu 710 | Ala | Met | Val | Glu | Ser 715 | Ile | Glu | Tyr | Arg | Arg 720 |
| Gln | Asn | Pro | Ser | Arg 725 | Cys | Ser | Val | Ser | Leu 730 | Ser | Asn | Val | Glu | Ala 735 | Arg |
| Arg | Phe | Phe | Asn 740 | Lys | Glu | Phe | Leu | Ser 745 | Lys | Pro | Lys | Ala | | | |